(12) United States Patent
Metzger

(10) Patent No.: US 8,591,593 B2
(45) Date of Patent: Nov. 26, 2013

(54) PIVOTING TIBIAL TRAY

(75) Inventor: Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 101 days.

(21) Appl. No.: 13/087,479

(22) Filed: Apr. 15, 2011

(65) Prior Publication Data

US 2012/0265317 A1    Oct. 18, 2012

(51) Int. Cl.
*A61F 2/38* (2006.01)

(52) U.S. Cl.
USPC ................... 623/20.32; 623/20.14

(58) Field of Classification Search
USPC .......... 623/20.14, 20.15, 20.16, 20.17, 20.21, 623/20.22, 20.23, 20.24, 20.25, 20.26, 623/20.27, 20.28, 20.29, 20.3, 20.31, 20.32, 623/20.33, 20.34
See application file for complete search history.

(56) References Cited

U.S. PATENT DOCUMENTS

| | | | |
|---|---|---|---|
| 4,136,405 A | | 1/1979 | Pastrick et al. |
| 4,883,488 A | | 11/1989 | Bloebaum et al. |
| 5,019,103 A | * | 5/1991 | Van Zile et al. ............ 623/20.34 |
| 5,370,693 A | * | 12/1994 | Kelman et al. ............ 623/16.11 |
| 5,549,689 A | | 8/1996 | Epstein et al. |
| 5,871,541 A | * | 2/1999 | Gerber ....................... 623/20.29 |
| 6,165,223 A | | 12/2000 | Metzger et al. |
| 6,217,618 B1 | | 4/2001 | Hileman |
| 6,506,216 B1 | * | 1/2003 | McCue et al. ............. 623/20.34 |
| 6,972,039 B2 | | 12/2005 | Metzger et al. |
| 7,037,341 B2 | * | 5/2006 | Nowakowski ............ 623/20.14 |
| 7,083,652 B2 | | 8/2006 | McCue et al. |
| 7,179,295 B2 | | 2/2007 | Kovacevic |
| 7,309,363 B2 | | 12/2007 | Dietz |
| 7,381,223 B2 | | 6/2008 | Kovacevic |
| 8,016,891 B2 | * | 9/2011 | Ensign ....................... 623/20.32 |
| 8,317,870 B2 | * | 11/2012 | Wagner et al. ............ 623/20.32 |
| 2006/0004460 A1 | * | 1/2006 | Engh et al. ................ 623/20.21 |
| 2006/0190087 A1 | * | 8/2006 | O'Connor et al. ........ 623/20.33 |
| 2007/0260322 A1 | * | 11/2007 | Nowakowski ............ 623/20.32 |
| 2009/0299482 A1 | | 12/2009 | Metzger et al. |
| 2010/0016978 A1 | | 1/2010 | Williams et al. |
| 2010/0100189 A1 | | 4/2010 | Metzger |
| 2010/0305710 A1 | | 12/2010 | Metzger et al. |

FOREIGN PATENT DOCUMENTS

EP    1582183 A1    10/2005

* cited by examiner

*Primary Examiner* — David Isabella
*Assistant Examiner* — Marcia Hoffman
(74) *Attorney, Agent, or Firm* — Harness, Dickey

(57) ABSTRACT

A tibial component for use with a resected tibia can include a medial tray portion adapted to engage a portion of the resected tibia and a lateral tray portion adapted to engage a portion of the resected tibia. A linkage can couple the medial tray portion to the lateral tray portion such that at least one of the medial tray portion and the lateral tray portion is pivotable relative to the other of the medial tray portion and the lateral tray portion to position the medial tray portion and the lateral tray portion at separate angles with respect to each other.

15 Claims, 4 Drawing Sheets

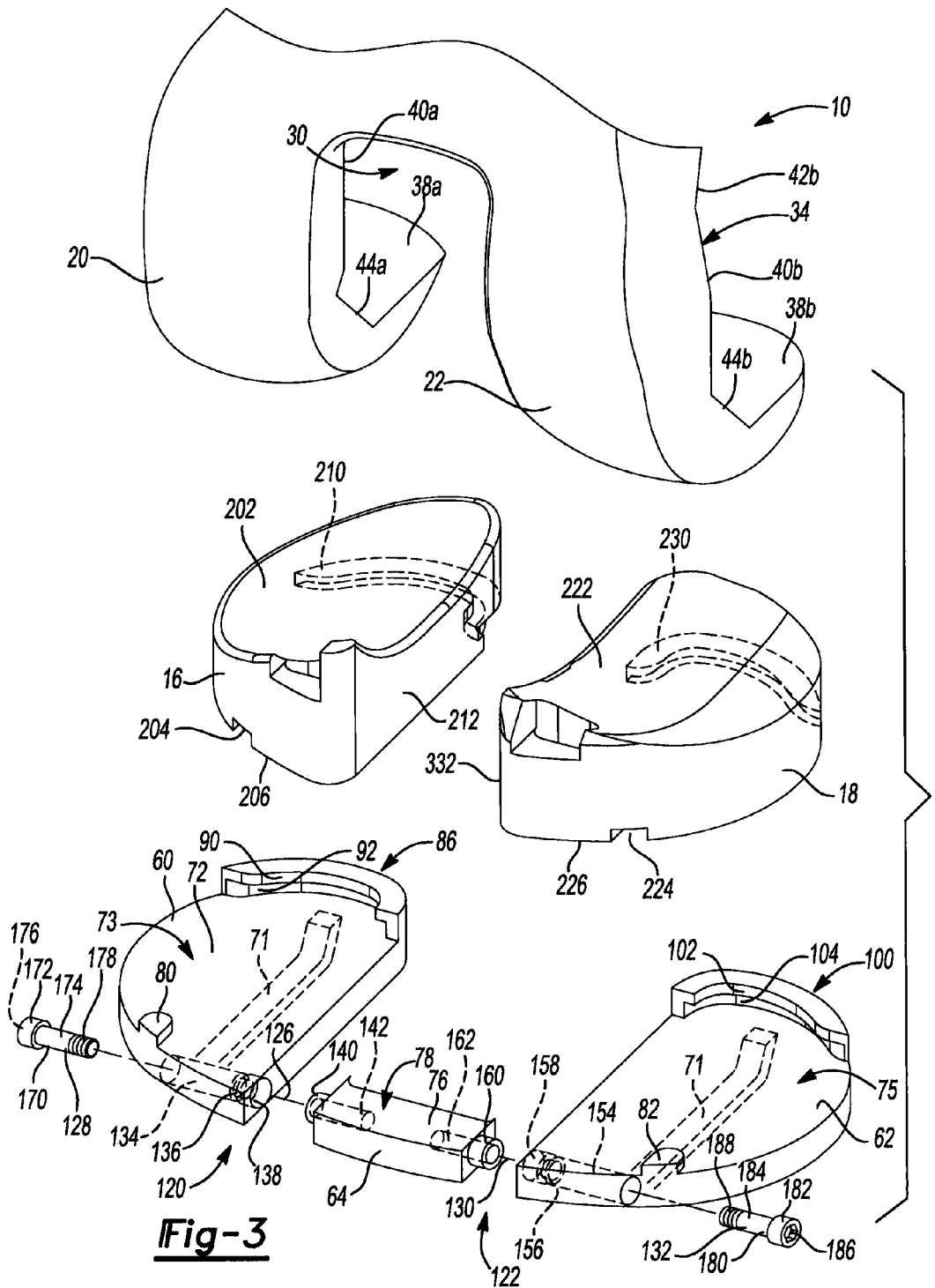

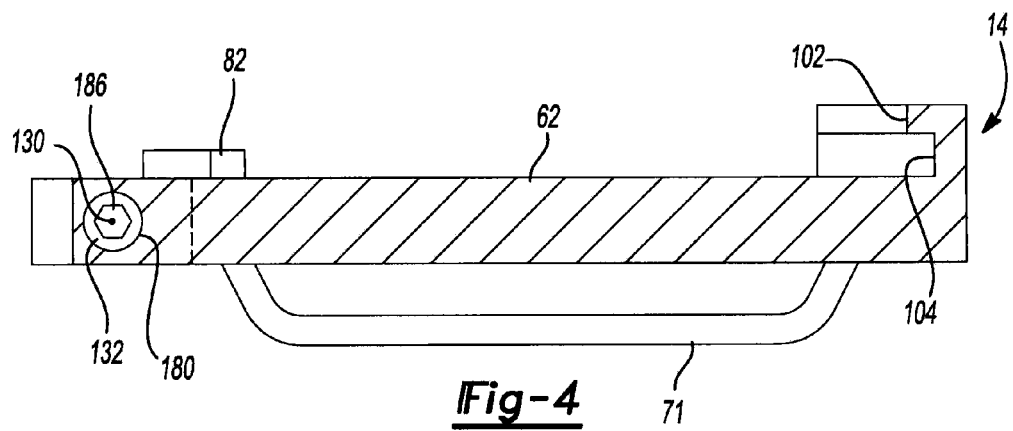
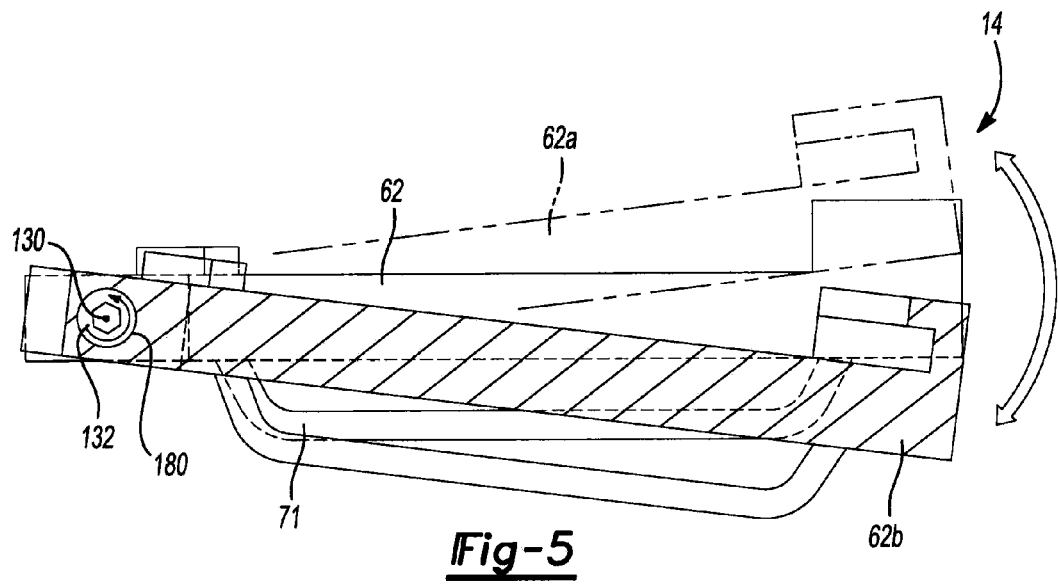

PIVOTING TIBIAL TRAY

FIELD

The present disclosure relates to a knee joint prosthesis including a tibial tray component having independent and selectively attachable bearings, the tibial tray including a medial tray portion and a lateral tray portion that are independently pivotal around axes that extend generally in a medial/lateral direction.

BACKGROUND

This section provides background information related to the present disclosure which is not necessarily prior art.

A knee joint prosthesis can generally comprise a femoral component and a tibial component. The femoral component and the tibial component can be designed to be surgically attached to the distal end of the femur and the proximal end of the tibia, respectively. The femoral component can further be designed to cooperate with the tibial component in simulating the articulating motion of an anatomical knee joint. In many examples, the tibial component can further include a bearing component that includes articulation surfaces on the medial and lateral side for cooperating with a medial and lateral condyle portion of the femoral component. In some examples, the bearing component can be fixed relative to the tibial component. In other examples, the bearing component can be a mobile bearing component that has at least a portion that can move relative to the tibial component during articulation of the femoral component. In some applications, it may be desirable to retain or reconstruct an anterior cruciate ligament (ACL) and/or a posterior cruciate ligament (PCL).

SUMMARY

This section provides a general summary of the disclosure, and is not a comprehensive disclosure of its full scope or all of its features.

A tibial component for use with a resected tibia can include a medial tray portion adapted to engage a portion of the resected tibia and a lateral tray portion adapted to engage a portion of the resected tibia. A linkage can couple the medial tray portion to the lateral tray portion such that at least one of the medial tray portion and the lateral tray portion is pivotable relative to the other of the medial tray portion and the lateral tray portion to position the medial tray portion and the lateral tray portion at separate angles with respect to each other.

According to additional features, the linkage can comprise a pivot axle that extends into one of the medial tray portion and the lateral tray portion. One of the medial tray portion and lateral tray portion is selectively rotatable around an axis defined by the pivot axle. The linkage can move between a locked position and an unlocked position. In the locked position, one of the medial tray portion and lateral tray portion is fixed relative to the other of the medial tray portion and lateral tray portion. In the unlocked position, one of the medial tray portion and lateral tray portion is rotatable relative to the other of the medial tray portion and lateral tray portion. In one example, the pivot axle comprises a threaded fastener.

According to still other features, a connection portion can be disposed between the medial and lateral tray portions. The connection portion, medial tray portion and lateral tray portion can collectively form a U-shaped body. The linkage can further comprise a first linkage and a second linkage. The first linkage can rotatably couple the medial tray portion to the connection portion. The second linkage can rotatably couple the lateral tray portion to the connection portion.

According to still other features, the pivot axle can further comprise a first pivot axle and a second pivot axle. The medial tray portion can define a medial bore that receives a first portion of the first pivot axle and the connection portion defines a medial receiving bore that receives a second portion of the first pivot axle. The lateral tray portion can define a lateral bore that receives a first portion of the second pivot axle and the connection portion can define a lateral receiving bore that receives a second portion of the second pivot axle. The first pivot axle can include a first threaded fastener that threadably engages the medial receiving bore. The second pivot axle can include a second threaded fastener that threadably engages the lateral receiving bore.

According to other examples, a medial bearing can be selectively engaged to the medial tray portion. A lateral bearing can be selectively engaged to the lateral tray portion. A femoral component can be adapted to engage a portion of a resected femur and be rotatably engaged with the medial and lateral bearings.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is an exploded perspective view of the knee prosthesis assembly of FIG. 1;

FIG. 4 is a lateral view of the pivoting tibial tray of FIG. 2;

Figure 6:
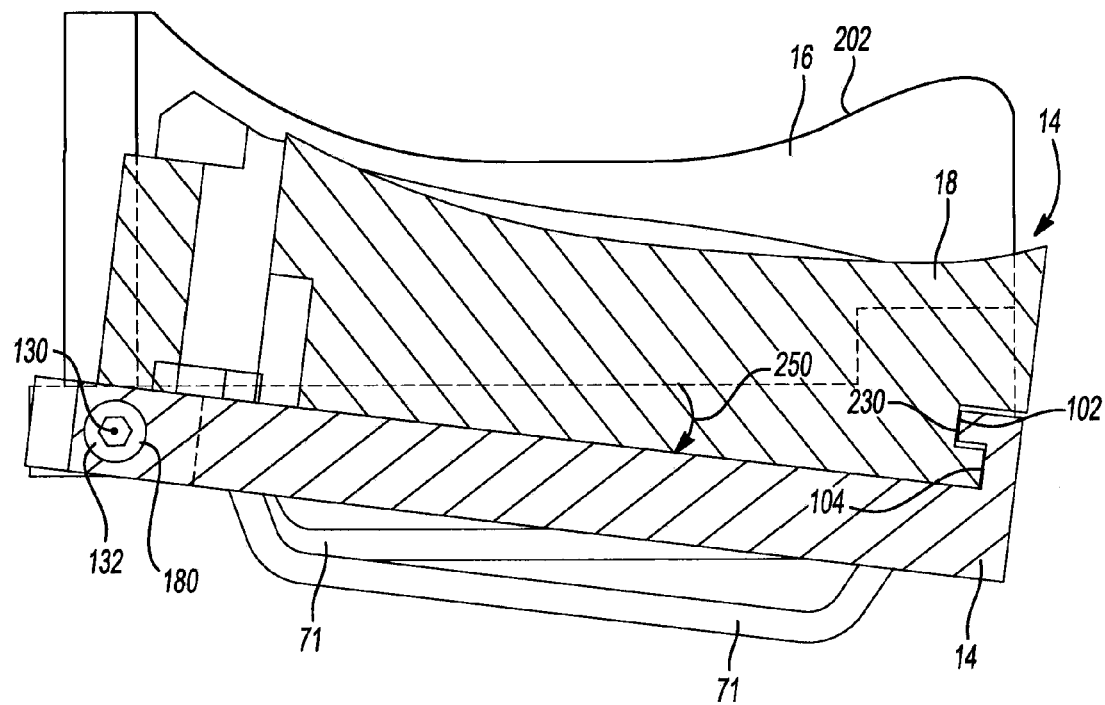

FIG. 5 is a lateral view of the pivoting tibial tray of FIG. 4 and shown with the lateral tray portion pivoted around a pivot axis that extends generally along a medial/lateral direction in an implanted position; and FIG. 6 is a lateral view of the pivoting tibial tray shown with a lateral bearing and a medial bearing connected to respective lateral and medial tray portions and shown with the lateral tray portion rotated generally posteriorly in an implanted position about the pivot axis.

Corresponding reference numerals indicate corresponding parts throughout the several views of the drawings.

DETAILED DESCRIPTION

Example embodiments will now be described more fully with reference to the accompanying drawings.

Figure 1:
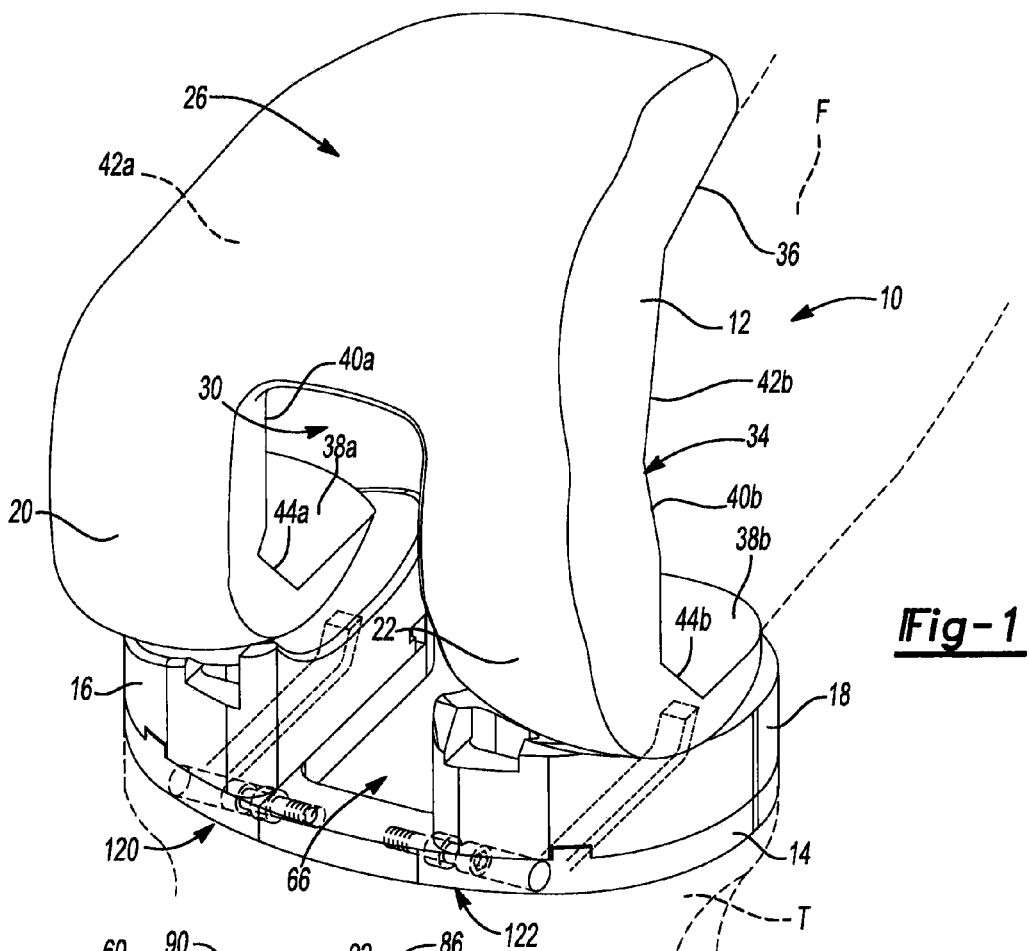
FIG. 1 is an anterior perspective view of a knee prosthesis assembly that incorporates a pivoting tibial tray according to one example of the present teachings.
Figure 2:
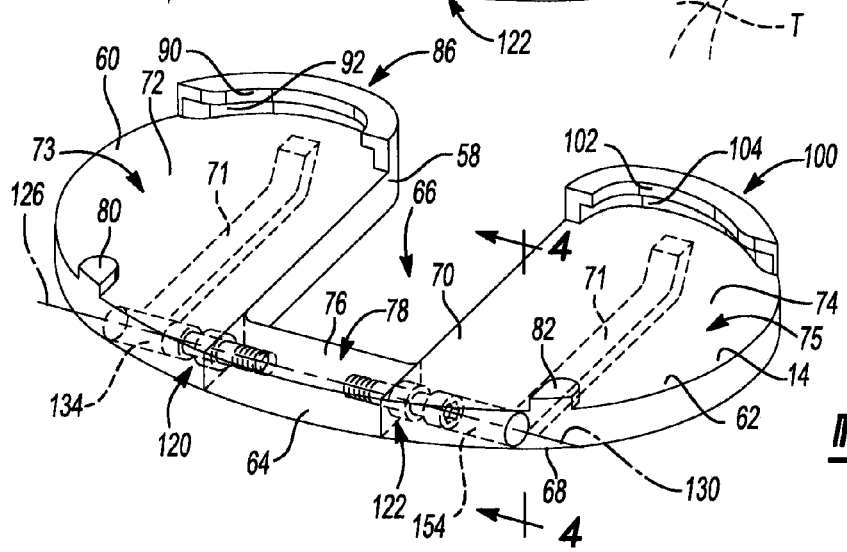
FIG. 2 is an anterior perspective view of the pivoting tibial tray of FIG. 1.

With initial reference to FIGS. 1 and 2, a knee prosthesis assembly constructed in accordance to one example of the present teachings is shown and generally identified at reference numeral 10. The knee prosthesis assembly 10 shown in the drawings is specific for a left knee. It will be understood, however, that a suitable right knee prosthesis can be similarly constructed. The knee prosthesis assembly 10 can generally include a femoral component 12, a tibial tray 14, a medial bearing 16, and a lateral bearing 18. As will be described, the knee prosthesis assembly 10 can be used when it is desirable to retain or reconstruct an ACL and/or a PCL.

The respective components of the knee prosthesis assembly 10 can be patient specific, such that each component can be constructed for optimal features of a given patient. For example, the bone interface margins of the femoral component 12 and tibial tray 14 can be patient specific for optimized bone coverage. In addition, the overall size, such as anterior-posterior dimensions and bone cut geometry can be determined and used for manufacturing the components of the knee prosthesis assembly 10. Moreover, some articulation features can be determined and used as criteria for forming the components of the knee prosthesis assembly 10. In sum, each of the components of the knee prosthesis assembly 10 can be patient-specific implant, a semi-custom implant, or an off-the-shelf or standard production implant.

A custom-made implant is a patient-specific, one-of-a-kind implant specifically made for a particular patient, and consequently, there is no inventory associated with such an implant. Standard or off-the-shelf implants are available and stocked in a number of sizes, typically six or more, and a number of configurations or types, including bilateral or unilateral implants, constrained, semi-constrained, mobile, etc. Because of the variety of sizes and configurations that are kept in stock to be accommodated by different patients, a large inventory of standard implants is created, and several molds for each type and size of implant may be used. Semi-custom implants can provide an intermediate solution between custom-made and off-the-shelf implants. Semi-custom implants reduce the size of inventory and molds required for production, while allowing some degree of patient-specific customization. Additional description of patient-specific implants and semi-custom implants and their implementations may be found in co-pending patent application Ser. No. 12/103,824, filed Apr. 16, 2008 and entitled: Method and Apparatus for Manufacturing an Implant, the disclosure of which is hereby incorporated by reference.

With specific reference now to FIG. 1, the femoral component 12 will now be described in greater detail. The femoral component 12 can generally comprise a cruciate retaining prosthesis and includes various portions to replace or mimic the distal femur. The femoral component 12 can include a medial condyle portion 20 and a lateral condyle portion 22. The condyle portions 20 and 22 can replace the medial and lateral condyles of a distal femur F. The medial and lateral condyle portions 20 and 22 can interconnect and be formed as a single piece with a patellar track portion 26. The patellar track portion 26 can allow for articulation of a patella, either natural or prosthetic patella, once the femoral component 12 is implanted onto the distal femur. The medial and lateral condyle portions 20 and 22 and the patellar track portion 26 can generally define an exterior portion of the femoral component 12. The femoral component 12 can define an opening or passage 30 between the medial and lateral condyle portions 20 and 22. As can be appreciated, the passage 30 can accommodate, and provide clearance for a host ACL and/or PCL or a reconstructed ACL and/or PCL.

The femoral component 12 can include a bone contacting or inferior surface 34 adapted to engage the distal femur F. The inferior surface 34 can include an anterior surface 36 that can be substantially flat and formed generally parallel to a pair of posterior surfaces 38a and 38b. A pair of intermediate surfaces 40a and 40b are provided generally at an intermediate portion of the inferior surface 34. A pair of angled anterior transition surfaces 42a and 42b generally connect the anterior surface 36 with the intermediate surfaces 40a and 40b, respectively. Similarly, a pair of angled posterior transition surfaces 44a and 44b are provided between the respective posterior surfaces 38a and 38b and the intermediate surfaces 40a and 40b. While not specifically shown, threaded bosses can be provided on each of the intermediate surfaces 40a and 40b, respectively. Similarly, threaded bosses can be provided on the posterior surfaces 38a and 38b, respectively. The bosses can be optionally used to threadably couple with various augments (not specifically shown) as necessary.

The femoral component 12 can be formed as a unitary structure and cast of a biocompatible high strength alloy, such as cobalt-chromium-molybdenum alloy or similar suitable material. All surfaces, which do not contact the femur F, can be highly polished to provide smooth articulating bearing surfaces. The interior surface 34 of the femoral component 12 can be roughened or uneven or include porous material to allow bone ingrowth or attachment with bone cement. Other features of the femoral component 12 can include those associated with the Oxford® Partial Knee marketed by Biomet, Inc.

With reference now to FIGS. 1-3, the tibial tray 14 will now be described in greater detail. The tibial tray 14 can include a generally U-shaped body 58 having a first or medial tray portion 60, a second or lateral tray portion 62, and a connection portion 64. A slot 66 can be formed in the tibial tray 14 generally between the medial and lateral tray portions 60 and 62. As with the passage 30 of the femoral component, the slot 66 of the tibial tray 14 can accommodate and provide a clearance for a host ACL and/or PCL or a reconstructed ACL and/or PCL. During implantation, the tibial tray 14 can be advanced posteriorly, such that the slot 66 can accommodate a host ACL and/or PCL. In instances where a reconstructed ACL and/or PCL is used, a tray (and bearing) having a passage can be utilized. One suitable configuration is further described in commonly owned U.S. Pat. No. 7,255,715; issued Aug. 14, 2007 and is hereby incorporated by reference.

The tibial tray 14 can include an inferior bone engaging side 68 and a superior bearing engaging side 70. A pair of fins 71 can extend from the inferior bone engaging side 68. While the fins 71 are shown operatively associated with the tibial tray 14, other structures suitable for engaging a proximal tibia T can include pegs, posts, or porous material and can additionally or alternatively be provided on the inferior bone engaging side 68. The medial tray portion 60 of the superior bearing engaging side 70 can include a medial tibial bearing engaging surface 72. The medial tibial bearing engaging surface 72 can extend generally along a plane 73. The lateral tray portion 62 of the superior engaging side 70 can include a lateral tibial bearing engaging surface 74. The lateral tibial bearing engaging surface 74 can extend generally along a plane 75. The connection portion 64 can have an upper surface 76 that extends along a plane 78.

The tibial tray 14 can generally include a locating tab 80 formed on an anterior edge of the medial tray portion 60 and a locating tab 82 formed on an anterior edge of the lateral tray portion 62. A retaining rail 86 can be formed around a posterior edge of the medial tray portion 60. The retaining rail 86 can include a lip 90 and a groove 92. A retaining rail 100 can be formed around a posterior edge of the lateral tray portion 62 of the tibial tray 14. The retaining rail 100 can generally include a lip 102 and a groove 104.

With particular reference now to FIGS. 2 and 3, additional features of the tibial tray 14 will now be described. The tibial tray 14 can include a first linkage 120 and a second linkage 122. As will be described further herein, the first linkage 120 and the second linkage 122 can allow a surgeon to selectively and independently pivot the medial tray portion 60 and lateral tray portion 62 relative to each other. In some examples, the medial tray portion 60 or lateral tray portion 62 can be pivoted relative to the connection portion 64. In this regard, the connection portion 64 can be aligned in various positions relative to either the medial tray portion 60 or the lateral tray portion 62. Explained further, the plane 78 of the connection portion 64 can be positioned coplanar with either, both, or neither of the planes 73 and 75. In other configurations, the connection portion 64 can be integrally formed with one of the medial or lateral tray portions 60, 62 when it is desirable to provide a tibial tray with only one linkage.

The medial tray portion 60 can rotate around a first or medial pivot axis 126 defined by a first or medial pivot axle 128 (FIG. 3). Similarly, the lateral tray portion 62 can pivot around a second or lateral pivot axis 130 defined by a second or lateral pivot axle 132. The first linkage 120 further includes a medial bore 134, a head engaging surface 136, and a medial recess 138 provided on the medial tray portion 60. The first linkage 120 further comprises a medial boss 140 and a medial receiving bore 142 provided on the connection portion 64. In an assembled position (FIG. 1), the medial boss 140 is received by the medial recess 138 to provide additional structural support to the first linkage 120. It is appreciated that alternate configurations may be provided. For example, the medial recess 138 may be formed on the connection portion 64 and the medial boss 140 may be formed on the medial tray portion 60.

The second linkage 122 can further comprise a lateral bore 154, a head engaging surface 156, and a lateral recess 158 provided on the lateral tray portion 62. The second linkage 122 can further include a lateral boss 160 and a lateral receiving bore 162 provided on the connection portion 64. In an assembled position (FIG. 1), the lateral boss 160 is received by the lateral recess 158 to provide structural support to the second linkage 122. It is appreciated that alternate configurations may be provided. For example, the lateral recess 158 may be formed on the connection portion 64 and the lateral boss 160 may be formed on the lateral tray portion 62.

The medial pivot axle 128 is in the form of a first or medial fastener 170 that includes a head 172 and a shaft 174. The head 172 defines a tool engaging portion 176. The shaft 174 can define threads 178. Similarly, the lateral pivot axle 132 can generally comprise a second or lateral fastener 180 having a head 182 and a shaft 184. The head 182 can define a tool engaging portion 186. The shaft 184 can include threads 188. As can be appreciated, the medial pivot axis 126 can be provided along the medial fastener 170. Similarly, the lateral pivot axis 130 can be provided along the lateral fastener 180. It will also be appreciated that while the medial pivot axis 126 and the lateral pivot axis 130 are represented in the drawings as coaxial relative to each other, they may alternatively be parallel and offset relative to each other, intersecting or non-parallel and non-intersecting.

With specific reference now to FIG. 3, the medial and lateral bearings 16 and 18 will be described. The medial bearing 16 can generally include a superior surface 202 that substantially conforms to and provides a surface contact with the profile of the medial condyle portion 20 of the femoral component 12. A channel 204 can be formed along an anterior inferior surface 206 and that generally tapers anteriorly. A groove 210 can be formed around a posterior edge of the bearing 16. The bearing 16 can have an inner wall 212 that cooperates with the U-shaped profile of the tibial tray 14 to accommodate a host or reconstructed ACL.

The lateral bearing 18 can generally include a superior surface 222 that substantially conforms to and provides a surface contact with the profile of the lateral condyle portion 22 of the femoral component 12. A channel 224 can be formed along an anterior inferior surface 226 and that generally tapers anteriorly. A groove 230 can be formed around a posterior edge of the lateral bearing 18. The lateral bearing 18 can have an inner wall 332 that cooperates with the U-shaped profile of the tibial tray 14 to accommodate a host or reconstructed ACL.

Connection of the medial bearing 16 to the medial tray portion 60 of the tibial tray 14 will now be discussed. Initially, the inferior surface 206 of the medial bearing 16 is located onto the medial tray portion 60 of the tibial tray 14. Next, the medial bearing 16 is slidably advanced posteriorly, such that the channel 204 slidably accommodates the locating tab 80 while the groove 210 locates under the lip 90. The medial bearing 16 is adapted to be statically secured relative to the medial tray portion 60 of the tibial tray 14 when assembled.

Connection of the lateral bearing 18 to the lateral tray portion 62 of the tibial tray 14 is similarly carried out. The medial bearing 16 and the lateral bearing 18 are both independently formed and interoperatively selected according to the needs of a given patient. It is appreciated that other configurations and connection techniques may be provided for the medial and lateral bearings 16 and 18. Furthermore, while the medial bearing 16 and the lateral bearing 18 are generally fixed bearing components, a mobile bearing component may be similarly provided for either of the medial and/or lateral sides. Further discussion of such mobile bearing components may be found in commonly owned and co-pending patent application Ser. No. 12/788,961; filed May 27, 2010, entitled Knee Prosthesis; the disclosure of which is incorporated herein by reference.

An exemplary method of rotating the lateral tray portion 62 of the tibial tray 14 relative to a remainder of the tibial tray 14 (i.e., the medial tray portion 60 and the connection portion 64) will now be described. At the outset, the lateral fastener 180 may be located into the lateral bore 154 such that the head 182 engages the head engaging surface 156 while the threads 188 are threadably received by the lateral receiving bore 162. A surgeon can advance a tool into the lateral bore 154 to engage the tool engaging portion 186 of the lateral fastener 180. The surgeon can then loosen the lateral fastener 180 such that the lateral tray portion 62 is free to rotate about the lateral pivot axis 130 in a first rotational direction (counter-clockwise as viewed in FIG. 5). Next, a surgeon can rotate the lateral tray portion 62 about the lateral pivot axis 130 such that the lateral tray portion 62 moves toward a generally anterior sloped position 62a (phantom line, FIG. 5). Alternatively, the surgeon can rotate the lateral tray portion 62 about the lateral pivot axis 130 in a second rotational direction (clockwise as viewed in FIG. 5) such that the lateral tray portion 62 moves toward a posterior sloped position 62b (solid line, FIG. 5) according to the needs of a particular patient. Once the lateral tray portion 62 has been rotated about the lateral pivot axis 130 to the desired position, the surgeon can then tighten the lateral fastener 180 into the lateral receiving bore 162 until the lateral tray portion 62 is statically fixed relative to the connection portion 64. It will be appreciated that the medial tray portion 60 may be rotated around the medial pivot axis 126 in a similar manner to independently position the medial tray portion 60 at a desired slope, if necessary. It is also appreciated that other mechanical configurations may be provided for the medial and second linkages 120, 122.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tibial component for use with a resected tibia comprising:
   a medial tray portion having a first inferior bone engaging side adapted to engage a portion of the resected tibia and a first superior bearing engaging side;
   a lateral tray portion having a second inferior bone engaging side adapted to engage a portion of the resected tibia and a second superior bearing engaging side;
   a connection portion between the medial and the lateral tray portions;
   a linkage that couples the medial tray portion to the lateral tray portion such that at least one of the medial tray portion and the lateral tray portion is pivotable relative to the other of the medial tray portion and the lateral tray portion to position the medial tray portion and the lateral tray portion at separate angles with respect to each other wherein (i) both of the first inferior bone engaging side and first superior bearing engaging side are concurrently pivotable with the medial tray portion and (ii) both of the second inferior bone engaging side and second superior bearing engaging side are concurrently pivotable with the lateral tray portion;
   a first pivot axle included with the linkage, the first pivot axle is removably coupled to each one of the medial tray portion and the connection portion; and
   a second pivot axle included with the linkage, the second pivot axle is removably coupled to each one of the lateral tray portion and the connection portion;
   wherein the first and second pivot axles are configured to move independently of one another.

2. The tibial component of claim 1, wherein the linkage is movable between a locked position wherein one of the medial tray portion and lateral tray portion is fixed relative to the other of the medial tray portion and lateral tray portion, and an unlocked position wherein one of the medial tray portion and lateral tray portion rotates relative to the other of the medial tray portion and lateral tray portion.

3. The tibial component of claim 2, wherein the linkage comprises a threaded fastener.

4. The tibial component of claim 1, wherein the medial tray portion defines a medial bore that receives a first portion of the first pivot axle and the connection portion defines a medial receiving bore that receives a second portion of the first pivot axle and wherein the lateral tray portion defines a lateral bore that receives a first portion of the second pivot axle and the connection portion defines a lateral receiving bore that receives a second portion of the second pivot axle.

5. The tibial component of claim 4 wherein the first pivot axle includes a first threaded fastener that threadably engages the medial receiving bore and the second pivot axle includes a second threaded fastener that threadably engages the lateral receiving bore.

6. The tibial component of claim 1, further comprising:
   a medial bearing that selectively engages the medial tray portion; and
   a lateral bearing that selectively engages the lateral tray portion.

7. A tibial component for use with a resected tibia comprising:
   a medial tray portion having a first inferior bone engaging side adapted to engage a portion of the resected tibia and a first superior bearing engaging side;
   a lateral tray portion having a second inferior bone engaging side adapted to engage a portion of the resected tibia and a second superior bearing engaging side;
   a connection portion disposed between the medial and lateral tray portions, the medial tray portion, lateral tray portion and connection portion collectively forming a generally U-shaped body; and
   a linkage that couples one of the medial tray portion and the lateral tray portion to the connection portion such that at least one of the medial tray portion and the lateral tray portion is pivotable relative to the other of the medial tray portion and the lateral tray portion to position the medial tray portion and the lateral tray portion at separate angles with respect to each other wherein (i) both of the first inferior bone engaging side and first superior bearing engaging side are concurrently pivotable with the medial tray portions and (ii) both of the second inferior bone engaging side and second superior bearing engaging side are concurrently pivotable with the lateral tray portion;
   a first pivot axle included with the linkage, the first pivot axle is removably coupled to each one of the medial tray portion and the connection portion; and
   a second pivot axle included with the linkage, the second pivot axle is removably coupled to each one of the lateral tray portion and the connection portion;
   wherein the first and second pivot axles are configured to move independently of one another.

8. The tibial component of claim 7, wherein the linkage is movable between a locked position wherein one of the medial tray portion and lateral tray portion is fixed relative to the other of the medial tray portion and lateral portion and an unlocked position wherein one of the medial tray portion and lateral tray portion rotates relative to the other of the medial tray portion and lateral tray portion.

9. The tibial component of claim 7, wherein the linkage comprises a threaded fastener.

10. The tibial component of claim 7, wherein the medial tray portion defines a medial bore that receives a first portion of the first pivot axle and the connection portion defines a medial receiving bore that receives a second portion of the first pivot axle.

11. The tibial component of claim 10 wherein the first pivot axle includes a first threaded fastener that threadably engages the medial receiving bore and the second pivot axle includes a second threaded fastener that threadably engages a lateral receiving bore.

12. The tibial component of claim 7, further comprising:
    a medial bearing that selectively engages the medial tray portion; and
    a lateral bearing that selectively engages the lateral tray portion.

13. A tibial component for use with a resected tibia comprising:
    a medial tray portion having a first inferior bone engaging side adapted to engage a portion of the resected tibia and a first superior bearing engaging side;
    a lateral tray portion having a second inferior bone engaging side adapted to engage a portion of the resected tibia and a second superior bearing engaging side;
    a connection portion disposed between the medial and lateral tray portions, the medial tray portion, lateral tray portion and connection portion collectively forming a generally U-shaped body;

a first linkage removably coupled to each one of the medial tray portion and the connection portion to couple the medial tray portion to the connection portion such that the medial tray portion is pivotable concurrently with the first inferior bone engaging side and first superior bearing engaging side relative to the lateral tray portion, the first linkage comprising a first threaded fastener that threadably engages the connection portion; and a second linkage removably coupled to each one of the lateral tray portion and the connection portion to couple the lateral tray portion to the connection portion such that the lateral tray portion is pivotable concurrently with the second inferior bone engaging side and second superior bearing engaging side relative to the medial tray portion, the second linkage comprising a second threaded fastener that threadably engages the connection portion, the first and the second fasteners are configured to move independently.

14. The tibial component of claim 13 wherein the medial tray portion defines a medial bore that receives a first portion of the first threaded fastener and the connection portion defines a medial receiving bore that receives a second portion of the first threaded fastener, wherein the lateral tray portion defines a lateral bore that receives a first portion of the second threaded fastener and the connection portion defines a lateral receiving bore that receives a second portion of the second threaded fastener, and wherein a medial bearing selectively engages the medial tray portion.

15. The tibial component of claim 14, further comprising:

a lateral bearing that selectively engages the lateral tray portion.

* * * * *